United States Patent [19]

Ward

[11] Patent Number: 4,604,398
[45] Date of Patent: Aug. 5, 1986

[54] BENZOQUINOLIZINE DERIVATIVES, AND THEIR USE AS $\alpha_2$ADRENOCEPTOR ANTAGONISTIC AGENTS

[75] Inventor: Terence J. Ward, Maidenhead, England

[73] Assignee: John Wyeth & Brother Limited, Maidenhead, England

[21] Appl. No.: 744,843

[22] Filed: Jun. 13, 1985

[30] Foreign Application Priority Data

Jun. 28, 1984 [GB] United Kingdom ............... 8416432

[51] Int. Cl.⁴ .................. A61K 31/435; C07D 455/06
[52] U.S. Cl. ........................................ 514/294; 546/95
[58] Field of Search ......................... 546/95; 514/294

[56] References Cited

U.S. PATENT DOCUMENTS 3,634,431 1/1972 VanDyke, Jr. ...................... 546/95

FOREIGN PATENT DOCUMENTS 1192520 7/1968 United Kingdom ................. 546/95

Primary Examiner—Henry R. Jiles
Assistant Examiner—J. Richter

Attorney, Agent, or Firm—George Tarnowski

[57] ABSTRACT

The invention concerns benzoquinolizines of general formula

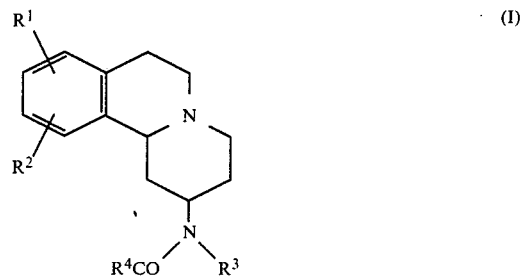

(I)

or their pharmaceutically acceptable acid addition salts. In the formula $R^1$ and $R^2$ which may be the same or different each represent hydrogen, lower alkyl, lower alkoxy or halogen, $R^3$ represents lower alkyl and $R^4$ is lower alkoxy or lower alkoxy carbonyl. The compounds possess $\alpha_2$-adrenoceptor antagonistic activity in warm blooded animals.

6 Claims, No Drawings

BENZOQUINOLIZINE DERIVATIVES, AND THEIR USE AS $\alpha_2$ ADRENOCEPTOR ANTAGONISTIC AGENTS The invention relates to certain novel benzoquinolizines, to processes for preparing the benzoquinolizines, to their use and to pharmaceutical compositions containing them.

The novel compounds of the present invention are benzoquinolizines of the general formula (I)

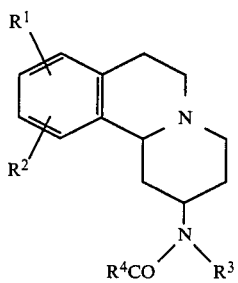

(I)

and their pharmaceutically acceptable acid addition salts. In formula (I), $R^1$ and $R^2$ which may be the same or different each represent hydrogen, lower alkyl, lower alkoxy or halogen, $R^3$ represents lower alkyl and $R^4$ is lower alkoxy or lower alkoxy carbonyl.

The term "lower" as used herein means that the radical referred to contain 1 to 6 carbon atoms. Preferably such radicals contains 1 to 4 carbon atoms. For example, a lower alkyl group may be methyl, ethyl, propyl or butyl and a lower alkoxy group may be methoxy, ethoxy, propoxy or butoxy. When $R^1$ and/or $R^2$ represents halogen the substituent may be, for example, fluorine, chlorine or bromine. Preferably both $R^1$ and $R^2$ are hydrogen.

Preferably $R^4$ is lower alkoxy.

The compounds of the invention may be prepared by reacting a reactive derivative of an acid of formula

 (II)

(where $R^4$ has the meaning given above) with a benzoquinolizine of the general formula

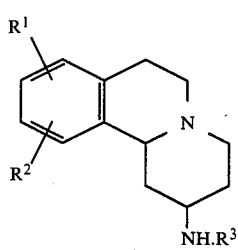 (III)

or an acid addition salt thereof (wherein $R^1$, $R^2$ and $R^3$ are as defined above) and, if required, converting a free base into a pharmaceutically acceptable acid addition salt. The reactive derivative of the acid can be, for example, the acid halide or anhydride. Preferably it is the acid halide, i.e. a compound of formula

 (V)

(where $R^4$ is as defined above and X is halogen, preferably chlorine). The reaction is generally carried out under basic conditions.

The starting materials of general formula (III) are known or can be prepared by known methods.

If in the process described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess two asymmetric carbon atoms and hence can exist in various stereochemical forms. In addition they can exist as cis or trans isomers. It will be realised that if the starting material of formula (III) is a mixture of isomers the product of formula (I) will also be a mixture of isomers unless the mixture is separated by standard procedures. The preferred compounds of the invention are the trans isomers in which the $-NR^3.COR^4$ group is in the equatorial position, i.e. compounds of the general formula (VI)

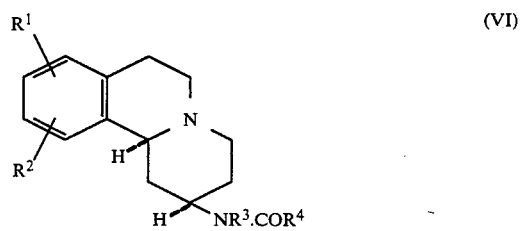

(VI)

and the pharmaceutically acceptable acid addition salts thereof. These compounds can be prepared by the methods described above from the corresponding trans isomer starting material. Resolution of a racemic final product or intermediate may be carried out by known procedures so as to give the product as an optically active enantiomorph.

The compounds of the present invention possess pharmacological activity. In particular the compounds possess $\alpha_2$-adrenoceptor antagonistic activity in warm blooded animals and hence are of value in conditions where antagonism of the $\alpha_2$-adrenoceptor is desirable, for example, as antidepressants, in treatment of diabetes and in inhibiting blood platelet aggregation.

The compounds of the invention are tested for $\alpha_2$-adrenoceptor antagonistic activity on the rat field stimulated vas deferens preparation using a modification of the method of Drew, Eur. J. Pharmac., 1977, 42, 123-130. The procedure is described below.

Desheathed vasa deferentia from sexually mature rats were suspended in a 6 ml organ bath in Krebs solution at 37° and bubbled with 5% $CO_2$ in oxygen. Platinum ring electrodes were positioned above and below the tissue for field stimulation, the stimulus parameters being 0.1 Hz 1 ms pulse width at supramaximal voltage. Twitch responses were recorded isotonically with a 0.5 g loading. Clonidine hydrochloride was used as the α-adrenoceptor agonist and cumulative concentration-response curves were constructed for the inhibition of twitch obtained with clonidine in the range 0.125 to 4 ng ml$^{-1}$. After washing out clonidine, the twitch response quickly recovered and an antagonist was then introduced into the Krebs reservoir. Clonidine concentration-response curves were repeated 90 min after introduction of the antagonist. The concentration of clonidine producing 50% inhibition of twitch before and after introduction of antagonist were obtained and the dose-ratio for clonidine was calculated. Various concentrations of the antagonists were used.

These results were plotted in the manner described by Arunlakshana & Schild, Br.J.Pharmac. Chemother., 1959, 14, 48–58 and the values of $pA_2$ and slope were calculated. The compounds of the invention possess potent $\alpha_2$-adrenoceptor antagonistic activity. For example, methyl{N-methyl-N-(1,3,4,6,7,11bα-hexahydro-2H-benzo[a]quinolizin-2β-yl)}carbamate, a representative compound of the invention, has been found to have a $pA_2$ for $\alpha_2$-adrenoceptor antagonistic activity of 7.87.

The compounds of the invention generally antagonise the $\alpha_2$-adrenoceptors to a much greater extent than the $\alpha_1$-adrenoceptors. The $\alpha_1$ antagonistic activity can be evaluated by a number of different methods. One method involves assessing the activity on the isolated anococcygeus muscle of the rat. The method is based on that of Gillespie, Br.J.Pharmac., 1972, 45, 404–416. In the procedure male rats (250–360 g) are killed by a blow on the head and bled. The two anococcygeus muscles are removed from their position in the midline of the pelvic cavity, where they arise from the upper coccygeal vertebrae. The muscles are suspended in 5 ml organ baths in Krebs solution containing $10^{-4}$M ascorbic acid, to prevent drug oxidation. The tissues are gassed with a 95% oxygen, 5% $CO_2$ mixture and maintained at 37°. Longitudinal muscle contractions are recorded using isotonic transducers. Cumulative dose response curves are then obtained to phenylephrine or in some cases methoxamine, both agents being presynaptic alpha adrenoceptor agonists. The concentration range of phenylephrine or methoxamine used is 0.02 to 0.8 μg.ml$^{-1}$. The agonist is then washed from the bath and the test drug added to the bathing medium at a concentration of $10^{-6}$M. After 30 min equilibration with the test drug a further agonist dose response curve is obtained. The washing, equilibration and agonists dosing procedures are then repeated using $10^{-5}$M and $10^{-4}$M solutions of the test drug. Estimates of the $pA_2$ value for the test drug as an antagonist of phenylephrine or methoxamine were made from the agonist dose-ratios using the method of Arunlakshana & Schild, Br. J. Pharmac. Chemother., 1959, 14, 48–58.

The $pA_2$ values for $\alpha_1$ antagonistic activity for methyl{N-methyl-N-(1,3,4,6,7,11bα-hexahydro-2H-benzo[a]quinolizin-2β-yl)}carbamate has been found to be 6.15 and the $\alpha_2/\alpha_1$ selectivity [i.e. antilog of ($\alpha_2 pA_2 - \alpha_1 pA_2$)] for this compound is 52.3.

The invention further provides a compound of formula I or a pharmaceutically acceptable acid addition salt for use in antagonising $\alpha_2$-adrenoceptors in a mammal. Also provided is the use of a compound of formula (I) or a pharmaceutically acceptable acid addition salt thereof for the manufacture of a medicament for use as an antidepressant, in the treatment of diabetes or in inhibiting blood platelet aggregation.

The invention also provides a pharmaceutical composition comprising a compound of general formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solibilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

Methyl{N-methyl-N-(1,3,4,6,7,11bα-hexahydro-2H-benzo[a]quinolizin-2β-yl)}carbamate An ice-cold, stirred solution of 2β-methylamino-1,3,4,6,7,11bα-hexahydro-2H-benzo[a]quinolizine (2.16 g) and triethylamine (1.15 g) in dichloromethane (25 cm$^3$) was treated slowly with a solution of methyl chloroformate (0.95 g) in dichloromethane (25 cm$^3$). The clear solution was kept at room temperature for 2 days, then washed with water (2×25 cm$^3$) and dried (MgSO$_4$). Filtration and evaporation afforded a red-brown oil (2.78 g) which was dissolved in hot methanol (5 cm$^3$) acidified with ethanolic HCl, diluted with methyl acetate (20 cm$^3$) and kept at 5° for 3 days. The crystals were collected by filtration and recrystallised twice from methanolmethyl acetate to give pure title compound as the hydrochloride threequarterhydrate (0.64 g), colourless microneedles, m.p. 163°–185° (dec).

EXAMPLE 2

Ethyl{N-Methyl-N-(1,3,4,6,7,11bα-hexahydro-2H-benzo[a]quinolizin-2β-yl)}carbamate A solution of ethyl chloroformate (0.62 g) in dichloromethane (25 cm$^3$) was added slowly to an ice-cold solution of 2β-methylamino-1,3,4,6,7,11bα-hexahydro-2H-benzo[a]quinolizine (1.08 g) and triethylamine (0.55 g) in dichloromethane (25 cm$^3$). The clear solution was stirred briefly at room temperature, then allowed to stand for 5 days when tlc showed essentially complete reaction. The mixture was washed with water (2×25 cm$^3$), dried (MgSO$_4$), filtered and evaporated to an orange-red syrup (1.46 g). This was dissolved in ethanol (3 cm$^3$), acidified with ethanolic hydrogen chloride, diluted with ethyl acetate (10 cm$^3$) and cooled. The precipitated crystals were collected by filtration and recrystallised twice from ethanol-ethyl acetate to give the title compound as the hydrochloride, quarterhydrate (0.75 g) after drying at 60°/1 ml (higher temperatures led to partial loss of HCl), m.p. 216°–218° (dec).

EXAMPLE 3

Ethyl{N-methyl-N-(1,3,4,6,7,11bα-hexahydro-2H-benzo[a]quinolizin-2β-yl)}oxamate

An ice-cold, stirred solution of 2β-methylamino-1,3,4,6,7,11bα-hexahydro-2H-benzo[a]quinolizine (2.16 g) and triethylamine (1.15 g) in dichloromethane (25 cm$^3$) was slowly treated with a solution of ethyl oxalyl chloride (1.36 g) in dichloromethane. The mixture was then kept at room temperature for 48 h, washed with water (2×25 cm$^3$) and dried (MgSO$_4$). Filtration and evaporation afforded a red-brown syrup (3.21 g). This was dissolved in ethanol (5 cm$^3$), acidified with ethanolic HCl and the solvent evaporated. The residual gum was crystallised from ethanol/ethyl acetate. The crystals were recrystallised twice from ethanol-ethyl acetate. The pale-yellow crystals of title compound, hydrochloride, hydrate (0.60 g) had m.p. 196°–212° (dec).

I claim

1. A compound selected from the group consisting of a benzoquinolizine of the formula

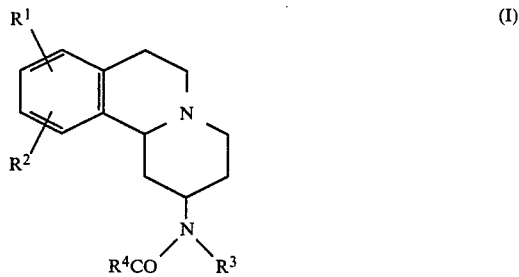

or a pharmaceutically acceptable acid addition salt thereof, wherein $R^1$ and $R^2$ which may be the same or different each represent hydrogen, lower alkyl, lower alkoxy or halogen, $R^3$ represents lower alkyl and $R^4$ is lower alkoxy or lower alkoxy carbonyl.

2. A compound according to claim 1 which is methyl{N-methyl-N-(1,3,4,6,7,11bα-hexahydro-2H-benzo[a]quinolizin-2β-yl)}carbamate or a pharmaceutically acceptable acid addition salt thereof.

3. A compound according to claim 1 which is ethyl{N-methyl-N-(1,3,4,6,7,11bα-hexahydro-2H-benzo[a]quinolizin-2β-yl)}carbamate or a pharmaceutically acceptable acid addition salt thereof.

4. A compound according to claim 1 which is ethyl{N-methyl-N-(1,3,4,6,7,11bα-hexahydro-2H-benzo[a]quinolizin-2β-yl)}oxamate or a pharmaceutically acceptable acid addition salt thereof.

5. A composition having $\alpha_2$-adrenoceptor antagonistic activity comprising an amount sufficient to antagonise $\alpha_2$-adrenoreceptors of a compound selected from the group consisting of a benzoquinolizine of the formula

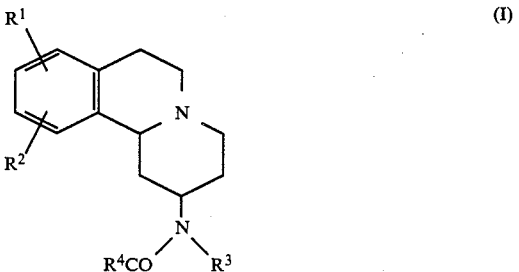

or a pharmaceutically acceptable acid addition salt thereof, wherein $R^1$ and $R^2$ which may be the same or different each represent hydrogen, lower alkyl, lower alkoxy or halogen, $R^3$ represents lower alkyl and $R^4$ is lower alkoxy or lower alkoxy carbonyl, in association with a pharmaceutically acceptable carrier.

6. A method of antagonising α6hd 2-adrenoreceptors in warm blooded animals which comprises administering to the animal an amount sufficient to antagonise $\alpha_2$-adrenoreceptors of a compound selected from the group consisting of a benzoquinolizine of the formula

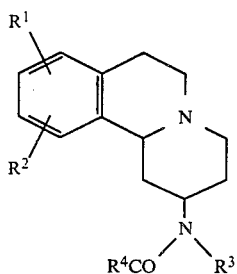 (I)

or a pharmaceutically acceptable acid addition salt thereof, wherein $R^1$ and $R^2$ which may be the same or different each represent hydrogen, lower alkyl, lower alkoxy or halogen, $R^3$ represents lower alkyl and $R^4$ is lower alkoxy or lower alkoxy carbonyl.

* * * * *

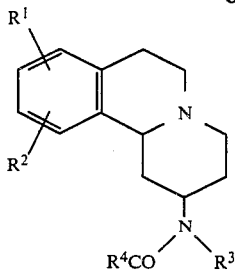 (I)

or a pharmaceutically acceptable acid addition salt thereof, wherein $R^1$ and $R^2$ which may be the same or different each represent hydrogen, lower alkyl, lower alkoxy or halogen, $R^3$ represents lower alkyl and $R^4$ is lower alkoxy or lower alkoxy carbonyl.

* * * * *